United States Patent [19]
Akram et al.

[11] Patent Number: 5,961,668
[45] Date of Patent: Oct. 5, 1999

[54] 4-(2,4-DIAMINOPHENOXYMETHYL)-1,3-DIOXOLANE SECONDARY INTERMEDIATES, PROCESSES FOR THEIR PRODUCTION, AND HAIR COLORANTS

[75] Inventors: Mustafa Akram, Hamburg; Wolfgang Bauer, Maintal; Andreas Bittner, Offenbach; Astrid Kleen, Duesseldorf, all of Germany

[73] Assignee: Hans Schwarzkopf GmbH & Co. KG, Hamburg, Germany

[21] Appl. No.: 09/043,394

[22] PCT Filed: Sep. 10, 1996

[86] PCT No.: PCT/EP96/03960

§ 371 Date: May 13, 1998

§ 102(e) Date: May 13, 1998

[87] PCT Pub. No.: WO97/10237

PCT Pub. Date: Mar. 20, 1997

[30] Foreign Application Priority Data

Sep. 15, 1995 [DE] Germany ............. 195 34 213

[51] Int. Cl.$^6$ ............. A61K 7/13; C07D 317/00
[52] U.S. Cl. ............. 8/409; 8/406; 8/416; 8/423; 8/576; 8/618; 8/624; 549/451
[58] Field of Search ............. 8/406, 408, 409, 8/411, 416, 423, 576, 618, 624; 549/451

[56] References Cited

U.S. PATENT DOCUMENTS

| | | | |
|---|---|---|---|
| 2,769,808 | 11/1956 | Tenebaum | 549/451 |
| 4,125,367 | 11/1978 | Bugaut et al. | 8/407 |
| 4,259,261 | 3/1981 | Bugaut et al. | 564/99 |
| 4,329,504 | 5/1982 | Bugaut et al. | 564/443 |

FOREIGN PATENT DOCUMENTS

| | | |
|---|---|---|
| 27 37 138 | 2/1978 | Germany . |
| 38 06 237 | 10/1989 | Germany . |
| 2 216 124 | 10/1989 | United Kingdom . |
| 93/10744 | 6/1993 | WIPO . |

OTHER PUBLICATIONS

Chemical Abstracts vol. 113, No. 21, Abs. No. 191208H, p. 710 (1990).
Chemistry of Synthetic Dyes, vol. V, Chap. VIII, pp. 475–533 (1971).
J. Soc. Cosmet. Chem 19: 361–79 (May 1968), Brody et al.
J. Soc. Cosmet. Chem 25: 131–138, Husemeyer (Mar. 1974).
Ber Dtsch. Chem. Ges. 28: 1167–1170 (1895).
J. Am. Chem Soc. 50: 2242–2249, Hill et al (Aug. 1928).
J. Am. Chem Soc. 67: 1621 (Sep. 1945).
J. Prakt. Chem. 44: 15–23 (1891), Otto.
J. Am. Chem Soc. 45: 785–790, Adams et al (Mar. 1923).
J. Am. Chem Soc. 45: 790–795, Pierce et al (Mar. 1923).

*Primary Examiner*—Caroline D. Liott
*Attorney, Agent, or Firm*—Ernest G. Szoke; Wayne C. Jaeschke; Glenn E.J. Murphy

[57] ABSTRACT

Compounds of the formula (I):

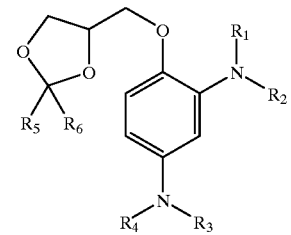

(I)

wherein $R_1$, $R_2$, $R_3$ and $R_4$ independently of one another may represent a hydrogen atom, a ($C_{1-4}$) alkyl group, a hydroxy ($C_{2-3}$) alkyl group, an alkoxy ($C_{2-3}$) alkyl group, an amino ($C_{2-3}$) alkyl group or a 2,3-dihydroxypropyl group and $R_5$ and $R_6$ independently of one another may represent hydrogen or a ($C_{1-4}$) alkyl group, are made by reacting 2,4-dinitrohalobenzenes with 4-hydroxymethyl-1,3-dioxolanes under alkaline conditions to form 4-(2,4-dinitrophenoxymethyl)-1,3-dioxolanes, which are further reduced to the compounds of formula (I). In an alternate process, the 4-hydroxymethyl-1,3-dioxolanes are reacted with 4-halo-3-nitranilines or 2-halo-5-nitranilines, the product further reacted first under basic conditions with chloroformic acid ester followed by treatment with strong base, alkylation or alkoxylation, reduction, and optionally further alkylation of alkoxylation to arrive at the compounds (I). The compounds are useful as secondary intermediates in oxidative dyeing of keratinous fibers, particularly hair, and can be incorporated into compositions of various forms suitable for dyeing such fibers.

13 Claims, No Drawings

4-(2,4-DIAMINOPHENOXYMETHYL)-1,3-DIOXOLANE SECONDARY INTERMEDIATES, PROCESSES FOR THEIR PRODUCTION, AND HAIR COLORANTS

BACKGROUND OF THE INVENTION

This invention relates to new substituted 4-(2,4-diaminophenoxymethyl)-1,3-dioxolanes corresponding to general formula (I):

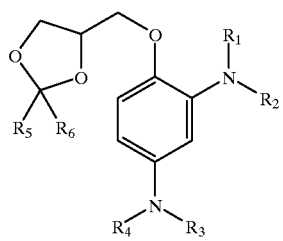

(I)

to processes for their production and to their use as hair colorants.

So-called oxidation dyes are used for coloring keratin fibers because they ultimately provide extremely fast intensive colors. Under boundary in-use conditions (low coloring temperature, short coloring time), they give fast, intensive colors. The actual dyes are formed by the oxidative coupling of a primary intermediate and a secondary intermediate during the coloring process. Numerous primary and secondary intermediates for obtaining various color tones, hereinafter referred to as hair dye intermediates, are described in the literature (K. Venkataraman, The Chemistry of Synthetic Dyes, Vol. V, Academic Press, 1971; F. Brody and M. S. Burns, J. Soc. Cosmet. Chem. 19, 361–379, 1968; H. Husemeyer, J. Soc. Cosmet. Chem. 25, 131–138, 1974).

Although in principle the oxidative coupling reaction, i.e. development of the color, can be carried out with atmospheric oxygen, it is generally too slow and/or provides uneven coloring results, so that chemical oxidizing agents are normally used. Preferred oxidizing agents are based on hydrogen peroxide and, besides hydrogen peroxide itself, on addition compounds thereof with urea, melamine or alkali metal perborate.

The use of 1-alkoxysubstituted 2,4-diaminobenzene derivatives as secondary intermediates is well known from the literature. Thus, DE-PS 38 06 237 and DE-OS 32 44 517 describe substituted 2,4-diaminoanisoles while DE-OS 27 37 138 describes substituted β-hydroxy-2,4-diaminophenetols. The colors described therein produced an intensive blue color tone, but with a distinct red component which is visible in particular in lighter shades. Where it is desired to obtain natural shades combining adequate depth of color with an adequate grey-masking effect, the red component is a disadvantage. Accordingly, there was an urgent need to develop new secondary intermediates which would give intensive colors in the clear blue range. It has now surprisingly been found that the compounds of general formula (I) described in the present invention satisfy this requirement particularly effectively.

DESCRIPTION OF THE INVENTION

Accordingly, the present invention relates to the use of compounds corresponding to formula (I):

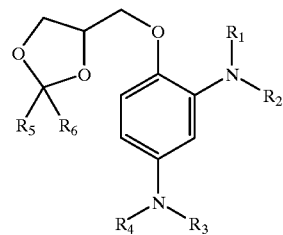

(I)

in which $R_1$, $R_2$, $R_3$ and $R_4$ independently of one another may represent a hydrogen atom, a $(C_{1-4})$ alkyl group, a hydroxy $(C_{2-3})$ alkyl group, an alkoxy $(C_{2-3})$ alkyl group, an amino $(C_{2-3})$ alkyl group or a 2,3-dihydroxypropyl group and $R_5$ and $R_6$ independently of one another may represent hydrogen or a $(C_{1-4})$ alkyl group, to processes for their production and to salts thereof with inorganic or organic acids.

The secondary intermediates according to the invention are prepared by reacting 2,4-dinitrohalobenzenes corresponding to formula (II), where X=flourine, chlorine, bromine or iodine, with 4-hydroxymethyl-1,3-dioxolanes corresponding to formula (III), where $R_5$ and $R_6$ are as defined above, in an alkaline reaction medium, optionally in the presence of phase transfer catalysts, to form 4-(2,4-dinitrophenoxymethyl)-1,3-dioxolanes corresponding to formula (IV) and reducing the compounds (IV) to form the compounds of formula (I) according to the invention:

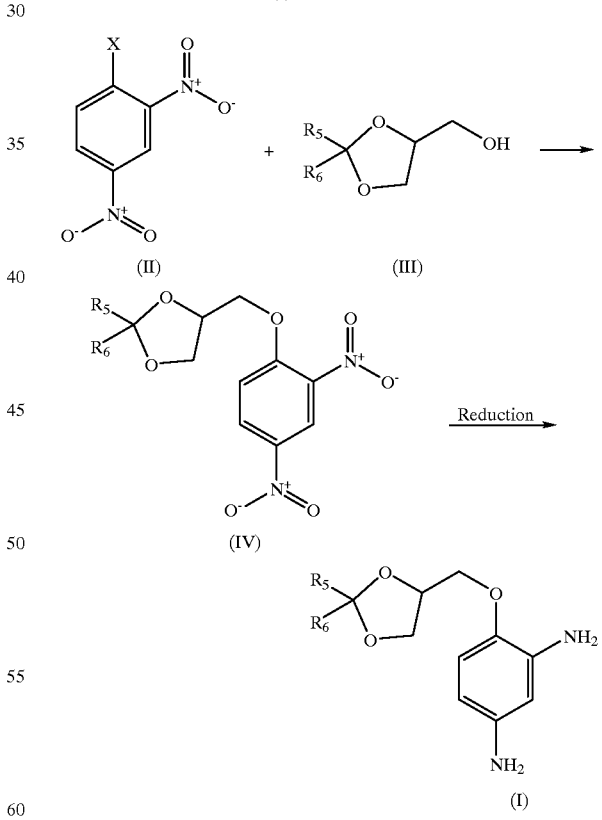

The compounds corresponding to formula (III) are already known and may be obtained by reaction of glycerol with carbonyl compounds (see, for example, E. Fischer, Ber. Dtsch. Chem. Ges. 28 1169 (1895); H. S. Hill, E. C. Hill and H. Hibbert, J. A. Chem. Soc. 50, 2246 (1928); M. S. Newman and M. Renoll, ibid 67, 1621 (1945)).

In another process, the secondary intermediates corresponding to formula (I) may be obtained by reacting 4-halo-3-nitranilines or 2-halo-5-nitranilines with 4-hydroxymethyl-1,3-dioxolanes in a first step to form a compound corresponding to formula (Va):

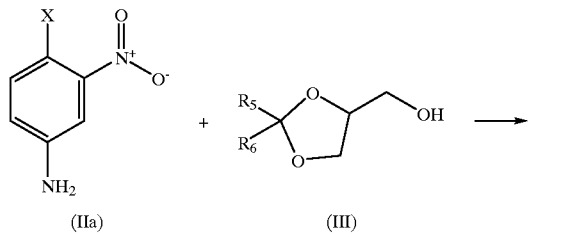

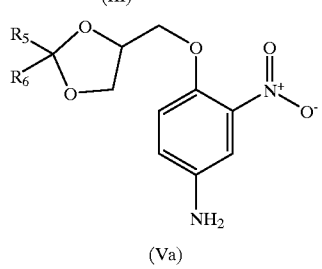

or formula (Vb):

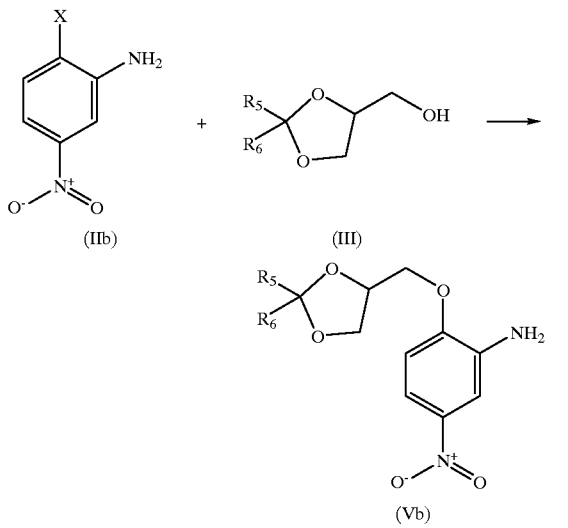

The compound (Va) or (Vb) thus obtained is then converted into a compound corresponding to formula (VIa):

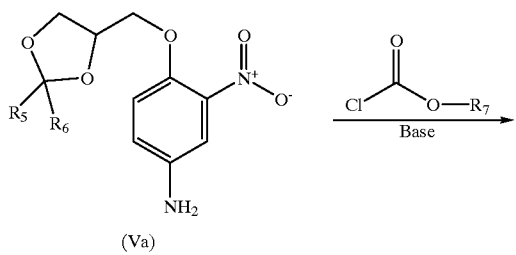

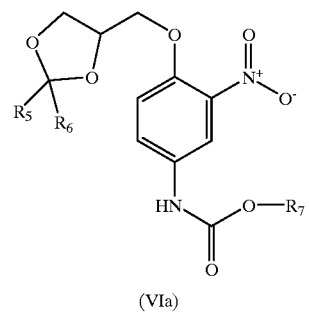

or formula (VIb):

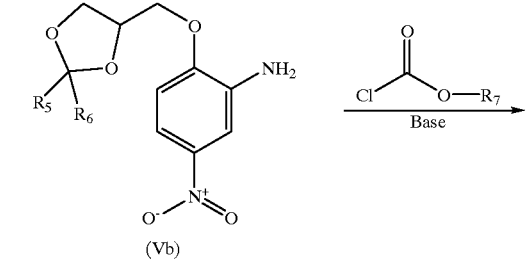

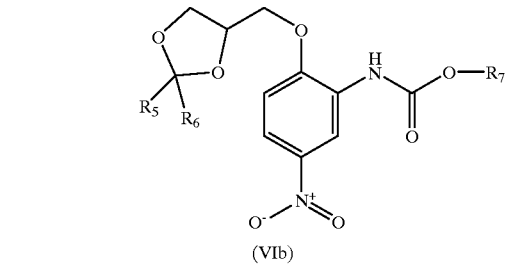

where $R_7$ represents $CH_2CH_2Cl$ or $CH_2CH_2CH_2Cl$, by reaction with chloroformic acid-2-chloroethyl ester or chloroformic acid-3-chloropropyl ester in an inert solvent. The intermediate product corresponding to formula (VIa) or (VIb) is then reacted with a strong base, for example sodium or potassium hydroxide, to form a compound corresponding to general formula (VIIa):

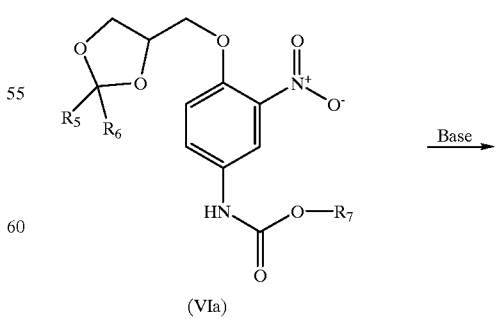

-continued

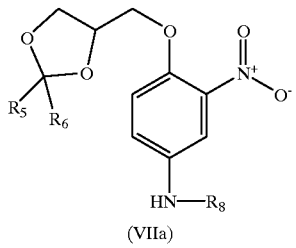

(VIIa)

or general formula (VIIb):

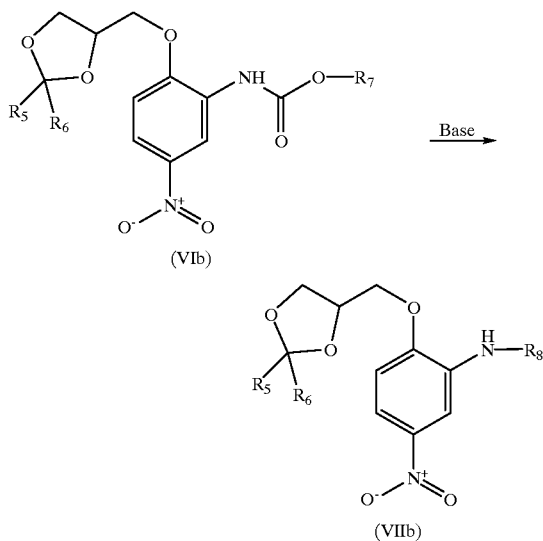

(VIb)

(VIIb)

where $R_8$ represents $CH_2CH_2OH$ or $CH_2CH_2CH_2OH$, which is then reacted with a known alkylating or alkoxylating agent to form an intermediate product corresponding to general formula (VIIIa) or (VIIIb):

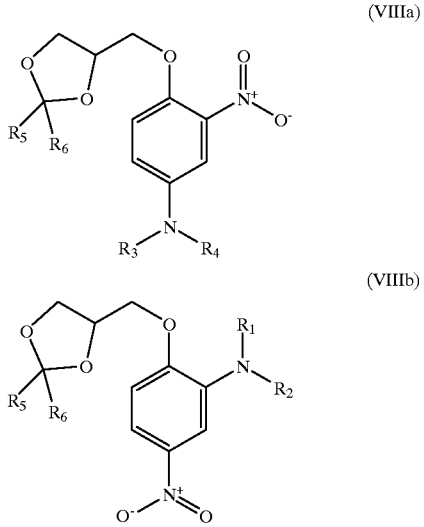

(VIIIa)

(VIIIb)

where $R_1$ to $R_4$ are as already defined.

After reduction and, optionally, further alkylation or alkoxylation, the secondary intermediates of (I) according to the invention are obtained and are optionally converted into a salt with an inorganic or organic acid.

For practical application as hair colorants, the hair dye intermediates are incorporated in a suitable cosmetic base which may be a solution, a creme, a foam or gel according to the nature of the desired end product. This preparation is mixed with the oxidizing agent immediately before application to the hair.

To obtained blue color tones, 1,3-diaminobenzene derivatives are mainly used as secondary intermediates and 1,4-diaminobenzene derivatives as primary intermediates. It has now been found that 4-(2,4-diaminophenoxymethyl)-1,3-dioxolanes corresponding to general formula (I) in combination with primary intermediates known per se give blue to blue-black colors combining surprisingly high strength of color with excellent fastness properties. These colors may be obtained by means of an oxidizing agent or by addition of a catalyst to the coloring preparation and subsequent oxidation with air (i.e. by leaving out the otherwise usual aqueous oxidizing agent based on hydrogen peroxide).

Known combinations of secondary intermediates and primary intermediates may be used for the hair colorants according to the invention. The following combinations represent preferred secondary intermediates and primary intermediates:

1. p-toluylenediamine, resorcinol, m-aminoaniline, 4-chlororesorcinol
2. p-toluylenediamine, 2-methyl resorcinol, 4-chlororesorcinol, 2-amino-3-hydroxypyridine
3. p-toluylenediamine, resorcinol, m-aminoaniline, p-aminoaniline, 2-hydroxy-4-aminotoluene
4. 3-methyl-4-aminoaniline, m-aminoaniline, 2-hydroxy-4-aminotoluene, 2-amino-3-hydroxypyridine
5. 3-methyl-4-aminoaniline, 2-methyl resorcinol, m-aminoaniline, p-toluylene-diamine, 2-hydroxy-4-aminotoluene, 2-amino-3-hydroxypyridine Accordingly, a particularly preferred embodiment of the invention is a hair colorant based on oxidation dyes which is characterized by 1. the use of new substituted 4-(2,4-diaminophenoxymethyl)-1,3-dioxolane derivatives,
2. the presence of a one-component hair coloring system,
3. the absence of any need to pretreat the hair with catalysts,
4. the addition of a catalyst to the coloring preparation,
5. the elimination of hydrogen peroxide as oxidizing agent,
6. transition metal salts and transition metal complexes, more particularly copper(II) chloride, copper(II) sulfate, or copper(II) acetate, or adducts thereof with ammonia, 1,2-ethylenediamine, phenanthroline, triphenyl phosphine, 1,2-diphenyl phosphinoethane, 1,3-diphenyl phosphinopropane or amino acids, for example (but not exclusively) glycine, leucine, methionine, alanine, phenyl alanine or proline, as catalyst for addition to the coloring preparation. The catalyst is preferably selected from the group consisting of copper (II)-1,2-diaminoethane chloride, copper (II)-1,10-phenanthroline chloride, copper (II)-tetraamine sulfate, copper (II)-glycinate, and mixtures thereof. The catalyst is present in the hair colorant in amounts 0.05% to 0.5% by weight.

The cosmetic base used for the hair colorant according to the invention is, for example a gel, a creme, a foam or a surfactant-containing solution, depending on the nature of the desired end product. The cosmetic base consists of the usual constituents—known from the prior art—suitable for application to the hair in the usual quantities. The constituents of such cosmetic bases are, for example, 1. wetting agents and emulsifiers
2. thickeners
3. reducing agents
4. perfume oils
5. hair-care additives and
6. solvents, for example water or lower alcohols.

The coloring of hair with the hair colorant according to the invention is carried out by applying the component diluted with water or undiluted to the hair and distributing it thereon. The necessary quantity of hair colorant—as well known to the expert—is dependent on the length of the hair to be colored. The application temperatures are preferably in the range from 15 to 40° C. while the contact time is preferably between 5 and 45 minutes and more preferably between 10 and 35 minutes. The hair colorant is then rinsed out from the hair, after which the hair is optionally washed with a shampoo, re-rinsed and then dried.

Compared with known hair colorants, the hair colorant according to the invention—in the particularly preferred embodiment—is easier to use, milder and more compatible through development of the color by oxidation with air rather than hydrogen peroxide in the presence of the catalyst added to the coloring preparation without any adverse effect on the coloring result.

The reaction of the compound corresponding to formula (Va) or (Vb) with a chloroformic acid-2-chloroethyl ester or chloroformic acid-3-chloropropyl ester is carried out on the lines of the known selective hydroxyalkylation of an amine with chloroformic acid chloroalkyl ester and subsequent basic treatment of the chloroalkyl carbamates (cf. Otto, J. Prakt. Chem. 44, 15, (1891); R. Adams and J. B. Segur, J. Am. Chem. Soc. 45, 785, (1923)). J. S. Pierce and R. Adams, J. Am. Chem. Soc. 45 790 (1923) describe in detail the reaction of the chloroformic acid chloroalkyl ester with primary aromatic amines. To form the compounds corresponding to general formula (VIa) or (VIb), the compound corresponding to formula (Va) or (Vb) is placed in an inert organic solvent, for example dioxane, $C_{1-4}$ alcohols, dimethyl formamide, tetrahydrofuran, toluene, chlorobenzene, methylethyl ketone, 1,2-dimethoxyethane, methyl-tert.butyl ether or diethylene glycol dimethyl ether and heated to a temperature between room temperature and the reflux temperature and preferably to a temperature between 30° C. and the reflux temperature. One of the chloroformic acid chloroalkyl esters mentioned is then added in an equimolar quantity or in a slight excess. The solvents may optionally be combined with water. An acid-binding agent may either be initially introduced with (Va) or (Vb) or added together with the chloroformic acid chloroalkyl ester already mentioned. Suitable acid-binding agents are bases, such as alkali metal hydroxides, hydrogen carbonates and carbonates, alkaline earth metal oxides, hydroxides, hydrogen carbonates and carbonates and tertiary organic amines. The reaction time is between 1 and 12 hours.

When the reaction is complete, the carbamates are isolated by a) introducing water or ice or a mixture of ice and water into the mixture with stirring or b) filtering off the inorganic salts and completely or partly distilling off the solvent, optionally with cooling, for example by addition of ice, so that the carbamates (VIa) or (VIb) formed precipitate substantially quantitatively in solid form.

The carbamates corresponding to general formula (VIa) or (VIb) are converted into the hydroxyalkyl compounds (VIIa) or (VIIb) by treatment with strong bases (alkali metal or alkaline earth metal hydroxides, preferably 10 to 50% sodium or potassium hydroxide). This may be done in two ways, namely:

a) The carbamate (VIa) or (VIb) is placed in water or an organic solvent, for example a $C_{1-4}$ alcohol, a water-miscible ether or mixtures thereof, after which the calculated quantity of hydroxide, i.e. 4 moles of hydroxide per mole of carbonate, is added at room temperature and the mixture is stirred until the reaction is complete, optionally with heating to the reflux temperature or addition of more hydroxide.
b) The hydroxide which may be diluted with the solvents mentioned is initially introduced, the carbamate corresponding to general formula (VIa) or (VIb) is added in pure form or in solution in one of the organic solvents mentioned at a temperature between room temperature and about 70° C. and the reaction mixture is stirred until the reaction is complete.

In both variants, the reaction solution, which has a pH value of about 12 to 14, may be basified to a pH value of about 5 to 10 for working up by addition of an organic or inorganic acid. The salts are then separated off, water is optionally added and the product corresponding to general formula (VIIa) or (VIIb) is isolated after removal of the organic solvent.

In both variants, the reaction time is distinctly shortened by addition of about 25 to 30% by weight of one of the above-mentioned organic solvents to the water-containing reaction mixture, the inorganic salts remaining dissolved in the reaction medium. The reaction takes about 1 to 12 hours.

The compounds corresponding to general formula (I) may be prepared by reduction of the compounds corresponding to general formula (Va) or (Vb), optionally after alkylation or alkoxylation, with base metals or by catalytic reduction.

Typical catalysts, for example Raney nickel, palladium on active carbon or platinum on active carbon, are used for the catalytic reduction. The reaction temperature is between room temperature and 120° C. and preferably between 35 and 100° C. while the pressure is between normal pressure and 100 bar and preferably between 20 and 70 bar. The solvent used may be selected from any of the usual solvents, such as water, toluene, glacial acetic acid, lower alcohols or ethers. After reduction and removal of the catalyst, the product corresponding to general formula (I) may be isolated in free form by distilling off the solvent in an inert gas atmosphere, optionally after alkylation or alkoxylation. Suitable alkylating agents are the known compounds dimethyl and diethyl sulfate while suitable alkoxylating agents are the known compounds ethylene oxide and propylene oxide. The product corresponding to general formula (I) is converted into a salt by addition of an approximately equivalent quantity of an acid, preferably in an inert gas atmosphere. The salt either precipitates directly or is obtained after removal of the solvent. Suitable inorganic acids for salt formation are, for example, hydrochloric acid, sulfuric acid and phosphoric acid while suitable organic acids are acetic acid, propionic acid, lactic acid or citric acid.

The following Examples are intended to illustrate the invention without limiting it in any way.

A. Production of the Catalysts

EXAMPLE A. 1

Preparation of copper(II) glycinate 1.8 g (9.8 mmoles) of copper(II) acetate are dissolved in 100 ml of hot methanol and a solution of 1.5 g (20 mmoles) of glycine in 50 ml of methanol is added with stirring to the resulting solution. The solution turns cloudy under the effect of precipitated product. After stirring for 2 hours at a falling temperature, the product precipitated is filtered off and dried. Yield: 2.5 g (96% of the theoretical), Mp.:>210° C.

EXAMPLE A. 2
Preparation of copper(II)-1,2-diaminoethane chloride 26.9 g (160 mmoles) of copper(II) chloride dihydrate are dissolved in 300 ml of hot methanol and a solution of 9.6 g (160 mmoles) of 1,2-diaminoethane in 100 ml of methanol is added with stirring. The solution turns cloudy under the effect of precipitated product. After stirring under reflux for 1 hour, the mixture is left to cool while stirring, the product precipitated is filtered off and dried. Yield: 12.5 g (40% of the theoretical), Mp.:>210°C.

B. Production of New Secondary Intermediates

All the compounds produced were characterized by IR or IR (KBr pellet) and $^1$H-NMR spectra (in $D_6$-DMSO). The IR spectrum data show only the very strong and strong bands. In the $^1$H-NMR spectrum data, s=singlet, d=doublet, dd=doublet of the doublet, t=triplet, m=multiplet, $^3$J and $^4$J=couplings by three or four bonds and $H^3$, $H^5$ and $H^6$=hydrogen atoms in positions 3, 5 and 6 of the benzene ring.

EXAMPLE B. 1
Preparation of 4-(2,4-dinitrophenoxymethyl)-2,2-dimethyl-1,3-dioxolane

Step a)
Preparation of 4-(2,4-dinitrophenoxymethyl)-2,2-dimethyl-1,3-dioxolane 204 g (1 mole) of 2,4-dinitrochlorobenzene are dissolved in a mixture of 650 ml of 1,2-dimethoxyethane, 528.6 g (4 moles) of isopropylidene glycerol and 7 g of methyl tri($C_{6-8}$)alkyl ammonium chloride. 123 g (1.1 mole) of 50% potassium hydroxide are added dropwise over a period of 1 hour with stirring and cooling at such a rate that the internal temperature does not rise above 35° C. The mixture is stirred overnight at room temperature and then stirred into 3250 ml of water. The product precipitated is filtered off under suction, washed twice with ca. 250 ml of water and dried in vacuo at 40° C.

Yield: 246.7 g (86.8% of the theoretical)
Melting point: 93–95° C.
IR: 3415 $cm^{-1}$ (vOH), 3122 $cm^{-1}$ (v $CH_{Ar}$), 2989, 2939 $cm^{-1}$ (v CH), 1612 $cm^{-1}$ (vC=C), 1537 $cm^{-1}$ ($v_{as}NO_2$), 1345 $cm^{-1}$ ($v_s NO_2$).

$^1$H-NMR: 8.76 ppm ($H^3$, d, $^4J_{H,H}$=2.81 Hz); 8.49 ppm ($H^5$, dd, $^3J_{H,H}$=9.33 Hz, $^4J_{H,H}$=2.81 Hz); 7.63 ppm ($H^6$, d, $^3J_{H,H}$=9.39 Hz); 4.48–4.34 ppm (3H, m, $\phi OCH_2CH$, $\phi OCH_2C\underline{H}$); 4.10 ppm (1H, syn-C$\underline{H}_2OC(CH_3)_2$, m), 3.82 ppm (1H, anti-C$\underline{H}_2OC(CH_3)_2$, m); 1.325 ppm (3H, s, syn-C$(CH_3)_2$); 1.308 ppm (3H, s, anti-C$(CH_3)_2$).

Step b)
Preparation of 4-(2,4-diaminophenoxymethyl)-2,2-dimethyl-1,3-dioxolane 215 ml of methanol are introduced into a 0.7 l autoclave, 85.3 g (0.3 mole) of 4-(2,4-dinitrophenoxymethyl)-2,2-dimethyl-1,3-dioxolane (step a) are dissolved therein and 0.6 g of palladium on active carbon 10% (Degussa) is added. After the autoclave has been closed and blanketed with nitrogen, hydrogenation is carried out under a pressure of 4 bar and at a temperature of 35 to 40° C. until no more hydrogen is taken up. 1.3 g of active carbon is added under nitrogen to the warm solution and the catalyst is filtered off. 42 g of 70% sulfuric acid are added dropwise to the solution while cooling with ice at 5° C. The product precipitated is filtered off under suction, washed with methanol and dried.

Yield: 68.9 g (68.3% of the theoretical)
Melting point: >250° C.
IR: 3415 $cm^{-1}$ (vOH), 3122 $cm^{-1}$ (v $CH_{Ar}$), 2989, 2939 $cm^{-1}$ (v $CH_{alkyl}$), 1612 $cm^{-1}$ (vC=C).

$^1$H-NMR: 8.76 ppm ($H^3$, d, $^4J_{H,H}$=2.81 Hz); 8.49 ppm ($H^5$, dd, $^3J_{H,H}$=9.33 Hz, $^4J_{H,H}$=2.81 Hz); 7.63 ppm ($H^6$, d, $^3J_{H,H}$=9.39 Hz); 4.48–4.34 ppm (3H, m, $\phi OCH_2CH$, $\phi OCH_2C\underline{H}$); 4.10 ppm (1H, m, syn-C$\underline{H}_2OC(CH_3)_2$); 3.82 ppm (1H, m, anti-C$\underline{H}_2OC(CH_3)_2$); 1.325 ppm (3H, s, syn-C$(CH_3)_2$); 1.308 ppm (3H, s, anti-C$(CH_3)_2$).

C. Coloring Examples

The hair colorants according to the invention are aqueous formulations. Aqueous formulations in the context of the invention are understood to be any formulations which contain water in any way such as, for example, cremes, emulsions, gels or even simple solutions. The compositions of the hair colorants are based on a mixture of the dye components with the additives typical of such cosmetic formulations. Typical additives in solutions, cremes, emulsions or gels are, for example, solvents, such as water, lower aliphatic alcohols, for example ethanol, propanol and isopropanol, or glycols, such as glycerol, and glycol ethers, such as propylene glycol; wetting agents or emulsifiers from the classes of anionic, cationic, amphoteric or nonionic surfactants, such as fatty alcohol sulfates, alkyl sulfonates, alkyl benzene sulfonates, alkyl trimethyl ammonium salts, alkyl betaines, ethoxylated fatty alcohols, ethoxylated nonyl fluorobenzenes, fatty acid alkanolamides, ethoxylated fatty acid esters; thickeners, such as higher fatty alcohols, starch, cellulose derivatives, vaseline, paraffin oil and fatty acids. The ingredients mentioned are used in the quantities typical of such applications, for example the wetting agents and emulsifiers in concentrations of about 0.5 to 30% by weight, while the thickeners may be present in the formulations in a quantity of about 0.1 to 25% by weight.

The hair colorants according to the invention can show a mildly acidic, neutral or alkaline reaction, depending on their composition. More particularly, they have a pH value in the alkaline range from 7.5 to 11.5 which is preferably adjusted with ammonia. However, organic amines, for example monoethanolamine and triethanolamine, or even inorganic bases, such as sodium hydroxide and potassium hydroxide, may also be used.

In procedures for the oxidative coloring of hair, the hair colorants according to the present invention, which contain a combination of known primary intermediates with at least one compound corresponding to general formula (I) as secondary intermediate and, optionally, known secondary intermediates and substantive dyes and, optionally, the catalysts already mentioned, or hair colorants to which no oxidizing agents are added before or during use, are applied to the hair. If desired, the colorants may be mixed with an oxidizing agent before application. Hydrogen peroxide (for example as a 6% aqueous solution) and addition compounds thereof with urea, melamine or sodium borate and mixtures of such hydrogen peroxide addition compounds with potassium peroxodisulfate is/are mainly used as the oxidizing agent for developing the hair color. The application temperatures are in the range from 15 to 40° C. After a contact time of about 10 to 30 minutes, the hair colorant is removed from the hair to be colored by rinsing. The hair may then be washed with a mild shampoo and dried.

The following Examples are intended to illustrate the invention without limiting it in any way.

EXAMPLE 1

| Hair coloring creme |
| --- |
| 2.20 g p-toluylenediamine sulfate |
| 3.36 g 4-(2,4-diaminophenoxymethyl)-2,2-dimethyl-1,3-dioxolane sulfate |
| 1.20 g oleic acid |
| 0.50 g sodium dithionite |
| 6.20 g lauryl alcohol diglycol ether sulfate, sodium salt (28% solution) |
| 18.0 g cetostearyl alcohol |
| 7.50 g ammonia, 25% |
| water to 100 g |

50 g of the hair colorant mentioned above are mixed just before use with 50 g of $H_2O_2$ solution (6%) in a ratio of 1:1 m/m and applied by brush to 100% grey hair. After a contact time of 30 minutes at room temperature, the colorant is rinsed out and the hair is dried. The hair has acquired a uniform deep blue color.

EXAMPLE 2

| Hair coloring gel |
| --- |
| 1.81 g p-phenylenediamine hydrochloride |
| 3.36 g 4-(2,4-diaminophenoxymethyl)-2,2-dimethyl-1,3-dioxolane sulfate |
| 12.0 g oleic acid |
| 12.0 g isopropanol |
| 5.00 g 4-nonoxynol |
| 10.0 g ammonia, 25% |
| 0.5 g sodium sulfite, water-free |
| water to 100 g |

50 g of the colorant mentioned above are mixed just before use with 50 g of hydrogen peroxide solution (6%). The mixture is applied to 100% grey hair and left thereon for 30 minutes at room temperature. The colorant is then rinsed out and, after shampooing, the hair is dried. The hair has acquired a blue-black color.

EXAMPLE 3

| Hair coloring creme |
| --- |
| 1.09 g p-aminophenol |
| 3.36 g 4-(2,4-diaminophenoxymethyl)-2,2-dimethyl-1,3-dioxolane sulfate |
| 2.50 g lauryl sulfate sodium sulfate (70% paste) |
| 1.00 g oleic acid |
| 0.60 g sodium sulfite, water-free |
| 12.0 g cetostearyl alcohol |
| 6.00 g myristyl alcohol |
| 1.00 g propylene glycol |
| 10.0 g ammonia, 25% |
| water to 100 g |

60 g of the colorant mentioned above are mixed just before use with 60 g of hydrogen peroxide solution (6%). The mixture is applied to 100% grey hair and left thereon for 30 minutes at room temperature. The colorant is then rinsed out and, after shampooing, the hair is dried. The hair has acquired a mid red-brown color.

EXAMPLE 4

| Hair coloring gel |
| --- |
| 2.20 g p-toluylenediamine sulfate |
| 3.36 g 4-(2,4-diaminophenoxymethyl)-2,2-dimethyl-1,3-dioxolane sulfate |
| 0.80 g 4-(3-hydroxypropylamino)-3-nitrophenol |
| 2.00 g oleic acid |
| 0.10 g polyacrylic acid |
| 0.50 g sodium sulfite, water-free |
| 4.0 g lauryl alcohol diglycol ether sulfate, sodium salt (28% solution) |
| 8.0 g ammonia, 25% |
| water to 100 g |

50 g of the colorant mentioned above are mixed just before use with 50 g of hydrogen peroxide solution (6%). The mixture is applied to 100% grey hair and left thereon for 30 minutes at room temperature. The hair colorant is then rinsed out and, after shampooing, the hair is dried. The hair has acquired a red-violet color.

EXAMPLE 5

| Hair-coloring gel |
| --- |
| 1.23 g 4-amino-3-methylphenol |
| 3.36 g 4-(2,4-diaminophenoxymethyl)-2,2-dimethyl-1,3-dioxolane sulfate |
| 1.00 g 4-amino-2-nitro-N-(2-hydroxyethyl)-aniline (HC Red 3) |
| 14.0 g oleic acid |
| 10.0 g isopropanol |
| 2.0 g PEG-3-cocamine |
| 0.5 g ascorbic acid |
| 8.0 g ammonia, 25% |
| water to 100 g |

50 g of the colorant mentioned above are mixed just before use with 50 g of hydrogen peroxide solution (6%). The mixture is applied to 100% grey hair and left thereon for 30 minutes at room temperature. The hair colorant is then rinsed out and, after shampooing, the hair is dried. The hair as acquired an intensive violet-red color.

EXAMPLE 6
(comparison with Example 1: oxidation with air and catalyst)

| Hair-coloring creme |
| --- |
| 2.20 g p-toluylenediamine sulfate |
| 3.36 g 4-(2,4-diaminophenoxymethyl)-2,2-dimethyl-1,3-dioxolane sulfate |
| 1.20 g oleic acid |
| 0.50 g sodium dithionite |
| 6.20 g lauryl alcohol diglycol ether sulfate, sodium salt (28% solution) |
| 18.0 g cetostearyl alcohol |
| 0.3 g copper(II) phenanthroline chloride |
| 7.50 g ammonia, 25% |
| water to 100 g |

50 g of the hair colorant mentioned above are mixed just before use with 50 g of water in a ratio of 1:1 m/m and applied by brush to 100% grey hair. After a contact time of 10 minutes at room temperature, the colorant is rinsed out and the hair is dried. The hair has acquired a uniform blue-silver grey color. The depth of the color obtained increases with the contact time.

EXAMPLE 7

(comparison with Example 1: oxidation with air but no catalyst)

| Hair-coloring creme |
| --- |
| 2.20 g p-toluylenediamine sulfate |
| 3.36 g 4-(2,4-diaminophenoxymethyl)-2,2-dimethyl-1,3-dioxolane sulfate |
| 1.20 g oleic acid |
| 0.50 g sodium dithionite |
| 6.20 g lauryl alcohol diglycol ether sulfate, sodium salt (28% solution) |
| 18.0 g cetostearyl alcohol |
| 7.50 g ammonia, 25% |
| water to 100 g |

50 g of the hair colorant mentioned above are mixed just before use with 50 g of water in a ratio of 1:1 m/m and applied by brush to 100% grey hair. After a contact time of 30 minutes at room temperature, the colorant is rinsed out and the hair is dried. The hair has not taken on any color under these conditions.

EXAMPLE 8

(comparison with Example 1: oxidation with $H_2O_2$ and catalyst)

| Hair-coloring creme |
| --- |
| 2.20 g p-toluylenediamine sulfate |
| 3.36 g 4-(2,4-diaminophenoxymethyl)-2,2-dimethyl-1,3-dioxolane sulfate |
| 1.20 g oleic acid |
| 0.50 g sodium dithionite |
| 6.20 g lauryl alcohol diglycol ether sulfate, sodium salt (28% solution) |
| 18.0 g cetostearyl alcohol |
| 0.3 g copper(II) phenanthroline chloride |
| 7.50 g ammonia 25% |
| water to 100 g |

50 g of the hair colorant mentioned above are mixed just before use with 50 g of $H_2O_2$ solution (6%) in a ratio of 1:1 m/m and applied by brush to 100% grey hair. After a contact time of 30 minutes at room temperature, the colorant is rinsed out and the hair is dried. The hair has acquired a uniform deep blue color.

Other secondary intermediates according to the invention corresponding to general formula (I)

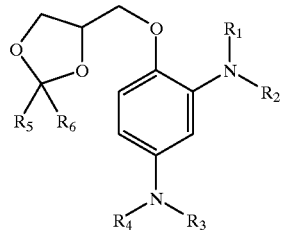

(I)

are listed in the following Table where the substituents $R_1$, $R_3$, $R_5$ and $R_6$ ($R_2$ and $R_4$ are always hydrogen in the cases indicated) are defined in columns 2 to 5 while the color obtained with p-toluylenediamine as in Example 1 is shown in column 6.

TABLE 1

Coloring of keratin fibers with other compounds in accordance with Example 1

| Example | $R_1$ | $R_3$ | $R_5$ | $R_6$ | Color |
| --- | --- | --- | --- | --- | --- |
| 1a | H | H | H | H | Blue-black |
| 1b | H | H | $CH_3$ | H | Blue-black |
| 1c | H | H | $C_2H_5$ | H | Blue-black |
| 1d | H | H | $CH(CH_3)_2$ | H | Blue-black |
| 1e | H | $CH_2CH_2OH$ | $CH_3$ | $CH_3$ | Blue-black |
| 1f | H | $CH_2CH_2CH_2OH$ | $CH_3$ | $CH_3$ | Blue-black |
| 1g | $CH_2CH_2OH$ | $CH_2CH_2OH$ | $CH_3$ | $CH_3$ | Blue-black |
| 1h | $CH_2CH_2CH_2OH$ | H | $CH_3$ | $CH_3$ | Blue-black |

We claim:

1. A compound of the formula (I):

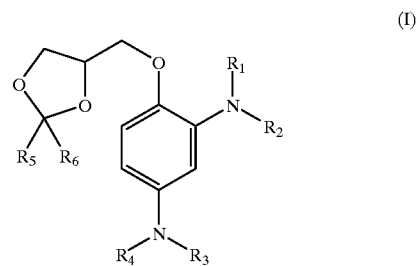

(I)

wherein $R_1$, $R_2$, $R_3$ and $R_4$ independently of one another may represent a hydrogen atom, a ($C_{1-4}$) alkyl group, a hydroxy ($C_{2-3}$) alkyl group, an alkoxy ($C_{2-3}$) alkyl group, an amino ($C_{2-3}$) alkyl group or a 2,3-dihydroxypropyl group and $R_5$ and $R_6$ independently of one another may represent hydrogen or a ($C_{1-4}$) alkyl group, and salts thereof with inorganic and organic acids.

2. A process for the production of a compound of the formula (I):

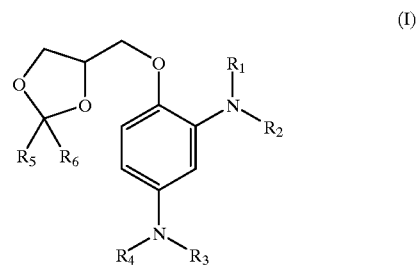

(I)

wherein $R_1$, $R_2$, $R_3$ and $R_4$ independently of one another may represent a hydrogen atom, a ($C_{1-4}$) alkyl group, a hydroxy ($C_{2-3}$) alkyl group, an alkoxy ($C_{2-3}$) alkyl group, an amino ($C_{2-3}$) alkyl group or a 2,3-dihydroxypropyl group and $R_5$ and $R_6$ independently of one another may represent hydrogen or a ($C_{1-4}$) alkyl group, said process comprising the steps of:

(a) reacting a 2,4-dinitrohalobenzene of the formula (II):

(II)

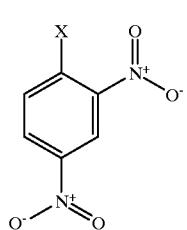

wherein X is F, Cl, Br or iodide, with a 4-hydroxymethyl-1,3-dioxolane of the formula (III):

(III)

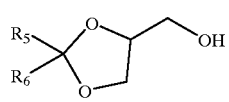

wherein $R_5$ and $R_6$ are as already defined, in an alkaline reaction medium to form a 4-(2,4-dinitrophenoxymethyl)-1,3-dioxolane of the formula (IV):

(IV)

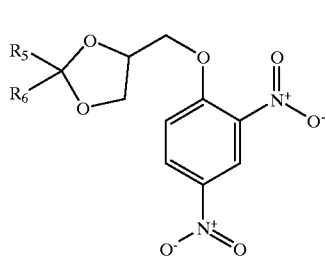

and (b) reducing the compound of formula (IV) to the compound of formula (I).

3. A process according to claim 2, further comprising the step of converting the compound of formula (I) to a salt with an inorganic or organic acid.

4. A process for the production of a compound of formula (I):

(I)

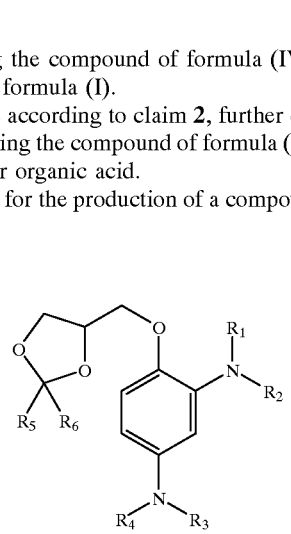

wherein $R_1$, $R_2$, $R_3$ and $R_4$ independently of one another may represent a hydrogen atom, a $(C_{1-4})$ alkyl group, a hydroxy $(C_{2-3})$ alkyl group, an alkoxy $(C_{2-3})$ alkyl group, an amino $(C_{2-3})$ alkyl group or a 2,3-dihydroxypropyl group and $R_5$ and $R_6$ independently of one another may represent hydrogen or a $(C_{1-4})$ alkyl group, said process comprising the steps of:

(a) reacting a compound of formula (IIa) or (IIb):

(IIa)

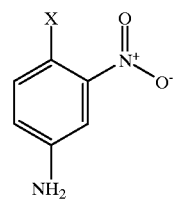

(IIb)

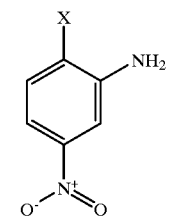

wherein X is F, Cl, Br or iodide, with a 4-hydroxy-1,3-dioxolane of the formula (III):

(III)

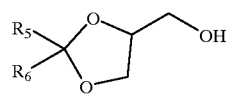

wherein $R_5$ and $R_6$ are as already defined, to form a compound of formula (Va) or (Vb):

(Va)

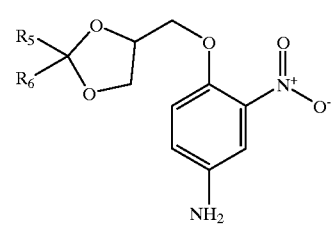

(Vb)

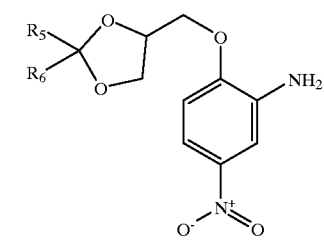

(b) reacting the compound of formula (Va) or (Vb) in an inert organic solvent with chloroformic acid-2-chloroethyl ester or chloroformic acid-3-chloropropyl ester to form a corresponding choroalkyl carbamate of formula (VIa) or (VIb):

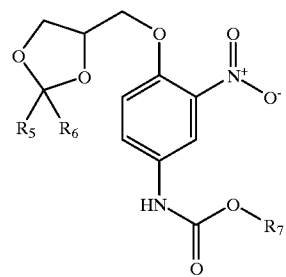
(VIa)

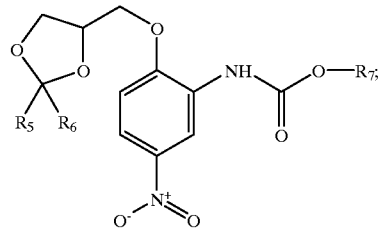
(VIb)

wherein $R_7$ is $CH_2CH_2Cl$ or $CH_2CH_2CH_2Cl$, (c) treating the compound of formula (VIa) or (VIb) with a strong base to form a compound of formula (VIIa) or (VIIb):

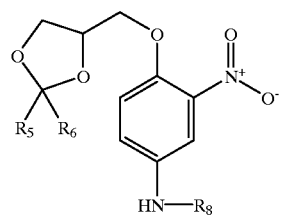
(VIIa)

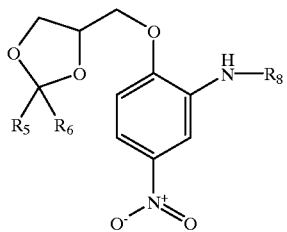
(VIIb)

wherein $R_8$ is 2-hydroxyethyl or 3-hydroxypropyl;

(d) reacting the compound of formula (VIIa) or (VIIb) with an alkylating agent or an alkoxylating agent to form a compound of formula (VIIIa) or (VIIIb):

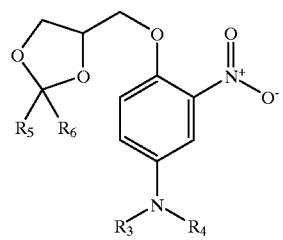
(VIIIa)

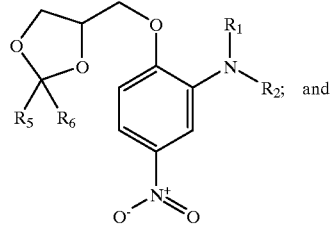
(VIIIb)

(e) reducing the compound of formula (VIIIa) or (VIIIb) to form the compound of formula (I).

5. A process according to claim 3, further comprising the step of converting the compound of formula (I) to a salt with an inorganic or organic acid.

6. A hair colorant comprising an effective amount of a secondary intermediate compound of formula (I):

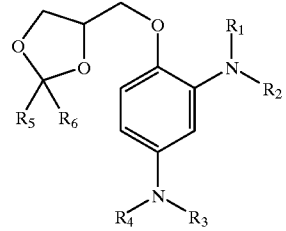
(I)

wherein $R_1$, $R_2$, $R_3$ and $R_4$ independently of one another may represent a hydrogen atom, a ($C_{1-4}$) alkyl group, a hydroxy ($C_{2-3}$) alkyl group, an alkoxy ($C_{2-3}$) alkyl group, an amino ($C_{2-3}$) alkyl group or a 2,3-dihydroxypropyl group and $R_5$ and $R_6$ independently of one another may represent hydrogen or a ($C_{1-4}$) alkyl group, and salts thereof with inorganic or organic acids.

7. A hair colorant according to claim 6, further comprising a primary intermediate compound.

8. A hair colorant according to claim 7, further comprising an oxidizing agent.

9. A hair colorant according to claim 8, further comprising an oxidation catalyst.

10. A hair colorant according to claim 9, wherein the oxidation catalyst is a transition metal salt or a transition metal complex.

11. A hair colorant according to claim 10, wherein the oxidation catalyst is selected from the group consisting of copper(II) chloride, copper(II) sulfate, copper(II) acetate, and adducts thereof with a compound selected from the group consisting of ammonia, 1,2-ethylenediamine, phenanthroline, triphenyl phosphine, 1,2-diphenyl phosphinoethane, 1,3-diphenyl phosphinopropane, amino acids, and mixtures thereof.

12. A hair colorant comprising an effective amount of a secondary intermediate compound of formula (I):

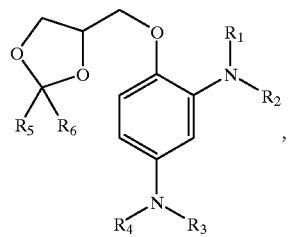

(I)

wherein $R_1$, $R_2$, $R_3$ and $R_4$ independently of one another may represent a hydrogen atom, a ($C_{1-4}$) alkyl group, a hydroxy ($C_{2-3}$) alkyl group, an alkoxy ($C_{2-3}$) alkyl group, an amino ($C_{2-3}$) alkyl group or a 2,3-dihydroxypropyl group and $R_5$ and $R_6$ independently of one another may represent hydrogen or a ($C_{1-4}$) alkyl group, and salts thereof with inorganic or organic acids, a primary intermediate compound, and an oxidation catalyst selected from the group consisting of copper(II)-1,2-diaminoethane chloride, copper(II)-1,10-phenanthroline chloride, copper(II)-tetraamine sulfate, copper(II)-glycinate, and mixtures thereof.

13. A hair colorant according to claim 12 comprising 0.05% to 0.5% by weight of the oxidation catalyst.

* * * * *